(12) United States Patent
Lee

(10) Patent No.: US 9,655,525 B2
(45) Date of Patent: May 23, 2017

(54) USER-WEARABLE DEVICES THAT MONITOR EXPOSURE TO BLUE LIGHT AND RECOMMEND ADJUSTMENTS THERETO

(71) Applicant: Salutron, Inc., Fremont, CA (US)

(72) Inventor: Yong Jin Lee, Seoul (KR)

(73) Assignee: SALUTRON INC., Newark, CA (US)

( * ) Notice: Subject to any disclaimer, the term of this patent is extended or adjusted under 35 U.S.C. 154(b) by 97 days.

(21) Appl. No.: 14/661,856

(22) Filed: Mar. 18, 2015

(65) Prior Publication Data
US 2016/0027282 A1  Jan. 28, 2016

Related U.S. Application Data

(60) Provisional application No. 62/029,253, filed on Jul. 25, 2014.

(51) Int. Cl.
| | |
|---|---|
| *A61B 5/00* | (2006.01) |
| *A61B 5/0205* | (2006.01) |
| *A61B 5/024* | (2006.01) |
| *A61B 5/11* | (2006.01) |

(52) U.S. Cl.
CPC .......... *A61B 5/0075* (2013.01); *A61B 5/4857* (2013.01); *A61B 5/681* (2013.01); *A61B 5/0205* (2013.01); *A61B 5/02416* (2013.01); *A61B 5/1118* (2013.01)

(58) Field of Classification Search
CPC ..... A61B 5/1118; A61B 5/681; A61B 5/0024; A61N 2005/0652; A61N 2005/0663; A61N 2005/0648; A61N 2005/0662; A61N 2005/0645; A61N 2005/0647; G01D 11/245
See application file for complete search history.

(56) References Cited

U.S. PATENT DOCUMENTS

| | | | |
|---|---|---|---|
| 2009/0240311 A1* | 9/2009 | Andersen | A61M 21/00 607/90 |
| 2010/0217358 A1* | 8/2010 | Hebert | A61M 21/00 607/88 |
| 2012/0271384 A1 | 10/2012 | Muehlemann | |
| 2013/0072765 A1* | 3/2013 | Kahn | A61B 5/01 600/301 |
| 2015/0192438 A1* | 7/2015 | Choi | G01D 11/26 73/431 |

(Continued)

*Primary Examiner* — Mirza Alam
(74) *Attorney, Agent, or Firm* — Vierra Magen Marcus LLP

(57) ABSTRACT

Described herein are user-wearable devices that include an optical sensor, and methods for use therewith. In certain embodiments, an optical sensor of a user-wearable device (e.g., a wrist-worn device) is used to detect blue light that is incident on the optical sensor and to produce a blue light detection signal indicative thereof, and thus, indicative of the response of the user's intrinsically photosensitive Retinal Ganglion Cells (ipRGCs). In dependence on the blue light detection signal, there is a determination of a metric indicative of an amount of blue light detected by the optical sensor. The metric is compared to a corresponding threshold, and a user notification is triggered in dependence on results of the comparing, wherein the user notification informs a person wearing the user-wearable device to adjust their exposure to light.

18 Claims, 10 Drawing Sheets

(56) References Cited

U.S. PATENT DOCUMENTS

2015/0342477 A1\* 12/2015 Hingorani .............. A61B 5/721
                                                            600/479
2015/0358201 A1\* 12/2015 Park ................... H04L 41/0813
                                                            715/735

\* cited by examiner

USER-WEARABLE DEVICES THAT MONITOR EXPOSURE TO BLUE LIGHT AND RECOMMEND ADJUSTMENTS THERETO

PRIORITY CLAIM

This application claims priority to U.S. Provisional Patent Application No. 62/029,253, filed Jul. 25, 2014, which is incorporated herein by reference.

This invention was made with government support under NASA Contract #NNX14CJ14P.

BACKGROUND

User-wearable devices, such as activity monitors or actigraphs, have become popular as a tool for promoting exercise and a healthy lifestyle. Such user-wearable devices can be used, for example, to measure heart rate, steps taken while walking or running and/or estimate an amount of calories burned. Additionally, or alternatively, a user-wearable device can be used to monitor sleep related metrics. User-wearable devices, such as smart watches, can additionally or alternatively be used to provide alerts to a user.

DETAILED DESCRIPTION

Figure 1A:
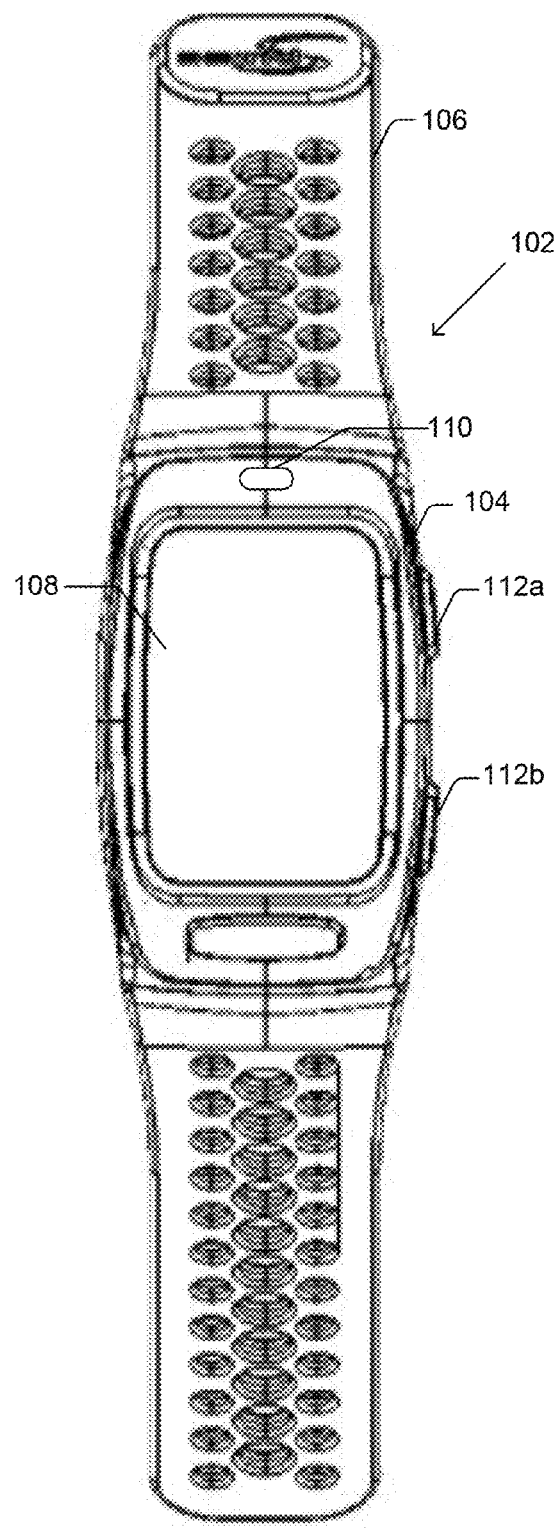
FIG. 1A depicts a front view of a user-wearable device, according to an embodiment.

In the following detailed description, reference is made to the accompanying drawings that form a part hereof, and in which is shown by way of illustration specific illustrative embodiments. It is to be understood that other embodiments may be utilized and that mechanical and electrical changes may be made. The following detailed description is, therefore, not to be taken in a limiting sense. In the description that follows, like numerals or reference designators will be used to refer to like parts or elements throughout. In addition, the first digit of a reference number identifies the drawing in which the reference number first appears.

Most mammals, including humans, coordinate their physiology and behavior in tune with a daily light cycle by utilizing a circadian clock that essentially keeps track of the time of day. To be effective as a time-keeper, circadian clocks require endogenous oscillations to be stably entrained (synchronized) to the external environmental schedule. Thus, the external environmental schedule (e.g., the light/dark cycle) provides important temporal information.

Several lines of evidence demonstrate that photoentrainment of circadian rhythms can occur in the absence of classical visual photoreceptors, which are the rods and cones in the retina of the mammalian eye. More specifically, it is now believed that non-imaging intrinsically photosensitive Retinal Ganglion Cells (ipRGCs) are a third class of retinal photoreceptors that play a major role in synchronizing circadian rhythms to the 24-hour light/dark cycle, including providing primarily length-of-day and length-of night information.

Intrinsically photosensitive Retinal Ganglion Cells (ipRGCs), which are also called photosensitive Retinal Ganglion Cells (pRGC), or melanopsin-containing retinal ganglion cells, are a type of neuron (nerve cell) in the retina of the mammalian eye. Unlike other retinal ganglion cells, ipRGCs are intrinsically photosensitive. Compared to the rods and cones, the ipRGCs have a slower response and signal the presence of light over the long term. The ipRGCs represent only a small percentage (approximately 1-3%) of the retinal ganglion cells.

As mentioned above, the ipRGCs play a major role in synchronizing circadian rhythms to the 24-hour light/dark cycle. The ipRGCs send light information via the retinohypothalamic tract directly to the circadian pacemaker of the brain, the suprachiasmatic nucleus (SCN) of the hypothalamus, which leads to a cascade of hormonal changes in the pituitary, pineal, adrenal and thyroid glands. The ipRGCs also contribute to the regulation of pupil size and other behavioral responses to ambient lighting conditions. Further, ipRGCs contribute to photic regulation of, and acute photic suppression of, release of the hormone melatonin from the pineal gland.

Disruption of circadian rhythms can result in a number of undesirable pathophysiological states in humans, including various sleep or circadian rhythm disorders, such as seasonal effect disorder (SAD) and insomnia. It would be beneficial if devices and methods were available to help avoid such disruptions to circadian rhythms.

The photopigment of ipRGCs, which is melanopsin, is excited by light mainly in the blue portion of the visible spectrum, with a peak absorption at approximately 480 nanometers (nm). In other words, the ipRGCs are primarily responsive to blue light. Specific embodiments of the present invention use an optical sensor that is adapted to detect blue light in order to provide a spectral response that is similar to the spectral response of ipRGCs. This is accomplished, for example, by covering one or more light detecting elements (also referred to as photodetectors) of an optical sensor with a filter that has a spectral response similar to the response of ipRGCs. The filter can be a blue organic filter, or a blue inorganic filter, or a combination thereof. The filter can alternatively be made from a plurality of layers of high and low refractive index inorganic dielectric films alternated one above the other to achieve the aforementioned desired spectral response. The filter can be a wafer level filter that is deposited, using a deposition process, above light detecting element(s). Alternatively, the filter can be manufactures independently of the light detecting element(s) and thereafter placed over the light detecting elements, e.g., during packing of the optical sensor. These are just a few examples of how filters can be used to provide an optical sensor that has a spectral response similar to the spectral response of ipRGCs, which examples are not meant to be all encompassing.

More specifically, certain embodiments of the present invention relate to a user-wearable device including an optical sensor having a spectral response that is similar to the spectral response of ipRGCs, and thereby, detects levels of blue light, and provides user notifications that inform a person wearing the user-wearable device to adjust their exposure to light. An example of such a user-wearable device will initially be described with reference to FIGS. 1A, 1B and 2.

FIG. 1A depicts a front view of a user-wearable device 102, according to an embodiment. The user-wearable device 102 can be a standalone device which gathers and processes data and displays results to a user. Alternatively, the user-wearable device 102 can wirelessly communicate with a base station (252 in FIG. 2), which can be a mobile phone, a tablet computer, a personal data assistant (PDA), a laptop computer, a desktop computer, or some other computing device that is capable of performing wireless communication. The base station can, e.g., include a health and fitness software application and/or other applications, which can be referred to as apps. The user-wearable device 102 can upload data obtained by the device 102 to the base station, so that such data can be used by a health and fitness software application and/or other apps stored on and executed by the base station.

The user-wearable device 102 is shown as including a housing 104, which can also be referred to as a case 104. A band 106 is shown as being attached to the housing 104, wherein the band 106 can be used to strap the housing 104 to a user's wrist or arm. Where the user-wearable device 102 includes the band 106, the device 102 can also be referred to as a wrist-wearable or wrist-worn device. The housing 104 is shown as including a digital display 108, which can also be referred to simply as a display. The digital display 108 can be used to show the time, date, day of the week and/or the like. The digital display 108 can also be used to display activity and/or physiological metrics, such as, but not limited to, heart rate (HR), heart rate variability (HRV), calories burned, steps taken and distance walked and/or run. The digital display 108 can also be used to display sleep metrics, examples of which are discussed below. Additionally, the digital display 108 can be used to display user notifications that inform a person wearing the user-wearable device to adjust their exposure to light. These are just a few examples of the types of information that may be displayed on the digital display 108, which are not intended to be all encompassing. As the terms are used herein, the terms user and person are used interchangeably.

The housing 104 is also shown as including an outward facing optical sensor 110 that includes one or more light detecting elements. Each such light detecting element can be, e.g., a photoresistor, photodiode, phototransistor, photo-darlington or avalanche photodiode, but is not limited thereto. The optical sensor 110 can be adapted to detect a narrow range of wavelengths corresponding to a specific color of light, such as blue light, and produce a light detection signal indicative thereof. Where the light detection signal is indicative of blue light, the light detection signal can be more descriptively referred to as a blue light detection signal. It is also possible that the optical sensor 110 is adapted to separately detect multiple different narrow ranges of wavelengths corresponding to multiple colors, such as, but not limited to, red (R), green (G) and blue (B), in which case the optical sensor can be referred to as an RGB sensor. Such an RGB sensor can produce three separate light detections signals, including a red light detection signal, a green light detection signal and a blue light detection signal. Such RGB sensors are commercially available from companies such as Maxim Integrated (headquartered in San Jose, Calif., USA), Intersil Corporation (headquartered in Milpitas, Calif., USA), and Texas Instruments Inc. (headquartered in Dallas, Tex., USA), just to name a few. It is also possible that the optical sensor is also configured to detect infrared (IR) light, in which case the optical sensor will also produce in IR light detection signal. Further, it is noted that the user-wearable device 102 can include more than one outwardly facing optical sensor 110. The outwardly facing optical sensor 110 can be specifically used to detect blue light in order to emulate the response of ipRGCs. The outwardly facing optical sensor 110 can also be used to detect whether it is daytime or nighttime, to determine whether a person is inside or outside, as well as for other purposes.

The housing 104 is further shown as including buttons 112a, 112b, which can individually be referred to as a button 112, and can collectively be referred to as the buttons 112. One of the buttons 112 can be a mode select button, while another one of the buttons 112 can be used to start and stop certain features. While the user-wearable device 102 is shown as including two buttons 112, more or less than two buttons can be included. The buttons 112 can additionally or alternatively be used for other functions. While the shapes of the housing 104 and the digital display 108 are shown as generally being rectangular, they can alternatively have other shapes, such as, but not limited to, circular or oval shapes.

In certain embodiments, the user-wearable device 102 can receive alerts from a base station (e.g., 252 in FIG. 2), or can generate its own alerts. For example, where the base station 252 is a mobile phone, the user wearable device 100 can receive alerts from the base station, which can be displayed to the user on the display 108. For a more specific example, if a mobile phone type of base station 252 is receiving an incoming phone call, then an incoming phone call alert can be displayed on the digital display 108 of the mobile device, which may or may not include the phone number and/or identity of the caller. Other types of alerts include, e.g., text message alerts, social media alerts, calendar alerts, medication reminders and exercise reminders, but are not limited thereto. Still other types of alerts can inform a user that they should adjust their exposure to light, as will be described in additional detail below. Such alerts can be generated solely by the user-wearable device 102, or with the assistance of a base station (e.g., 252) with which the user-wearable device 102 wirelessly communicates. The user-wearable device 102 can inform the user of a new alert by vibrating and/or emitting an audible sound.

Figure 1B:
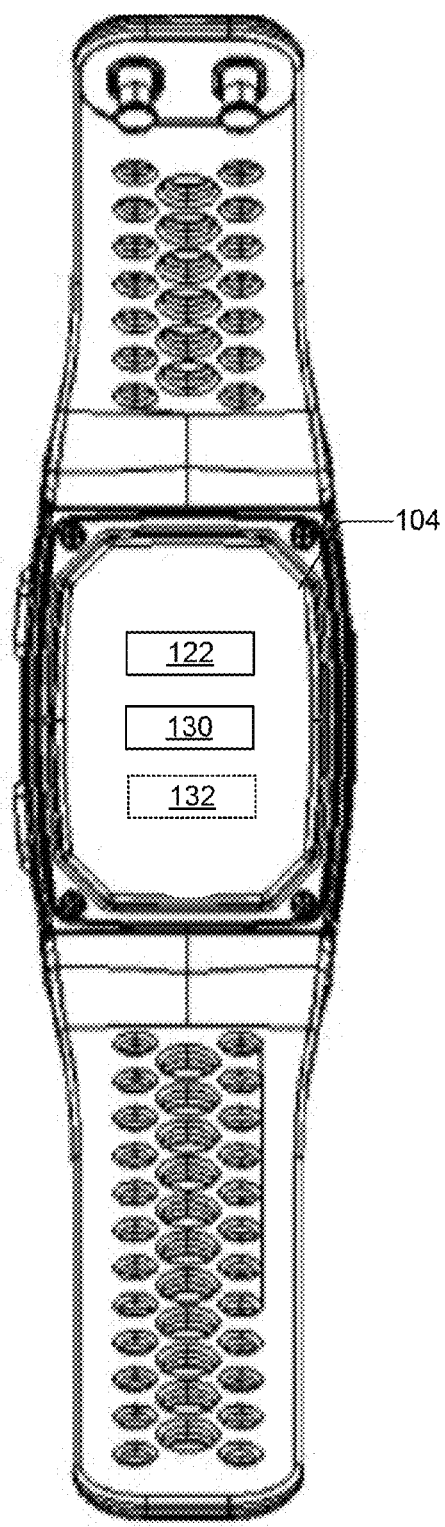
FIG. 1B depicts a rear view of the user-wearable device of FIG. 1A, according to an embodiment.

FIG. 1B illustrates a rear-view of the housing 104 of the user-wearable device 102. Referring to FIG. 1B, the backside of the housing 104 includes an optical sensor 122 and a skin temperature sensor 130. It is also possible that the user-wearable device 102 includes less sensors than shown, more sensors than shown and/or alternative types of sensors. For example, the user-wearable device 102 can also include one or more type of motion sensor 132, which is shown in dotted line because it is likely completely encased with the housing 104.

In accordance with an embodiment, the optical sensor 122 includes both a light source and a light detector, in which case the optical sensor 122 can be used as a photoplethysmography (PPG) sensor, and in which case the optical sensor 122 can also be referred to as a PPG sensor 122. The light source of the optical sensor 122 can include one or more light emitting elements, each of which can be a light emitting diode (LED), incandescent lamp or laser diode, but is not limited thereto. While infrared (IR) light sources are often employed in optical sensors, because the human eye cannot detect IR light, the light source can alternatively produce light of other wavelengths. The light detector of the optical sensor 122 can include one or more light detecting elements. Such light detecting elements can be, e.g., a photoresistor, photodiode, phototransistor, photodarlington or avalanche photodiode, but is not limited thereto. In accordance with specific embodiments, the optical sensor 122 can also be used to detect heart rate (HR) and heart rate variability (HRV). More specifically, when operating as a PPG sensor, the light source of the optical sensor 122 emits light that is reflected or backscattered by patient tissue, and reflected/backscattered light is received by the light detector of the optical sensor 122. In this manner, changes in reflected light intensity are detected by the light detector, which outputs a PPG signal indicative of the changes in detected light, which are indicative of changes in blood volume. The PPG signal output by the light detector can be filtered and amplified, and can be converted to a digital signal using an analog-to-digital converter (ADC), if the PPG signal is to be analyzed in the digital domain. Each cardiac cycle in the PPG signal generally appears as a peak, thereby enabling the PPG signal to be used to detect peak-to-peak intervals, which can be used to calculate heart rate (HR) and heart rate variability (HRV). In accordance with certain embodiments, the optical sensor 122 includes a light source that emits light of two different wavelengths that enables the optical sensor 122 to be used as a pulse oximeter, in which case the optical sensor 122 can non-invasively monitor the arterial oxygen saturation of a user wearing the user-wearable device 102.

Depending upon implementation, heart rate (HR) and heart rate variability (HRV) can be detected based on signals obtained by the PPG sensor 122. HR and/or HRV can be automatically determined continuously, periodically or at other specified times or based on a manual user action. For example, in a free living application, HR can be determined automatically during periods of interest, such as when a significant amount of activity is detected.

The skin temperature sensor 130 can be implemented, e.g., using a thermistor, and can be used to sense the temperature of a user's skin, which can be used to determine user activity and/or calories burned.

In accordance with an embodiment the motion sensor 132 is an accelerometer. The accelerometer can be a three-axis accelerometer, which is also known as a three-dimensional (3D) accelerometer, but is not limited thereto. The accelerometer may provide an analog output signal representing acceleration in one or more directions. For example, the accelerometer can provide a measure of acceleration with respect to x, y and z axes. The motion sensor 132 can alternatively be a gyrometer, which provides a measure of angular velocity with respect to x, y and z axes. It is also possible that the motion sensor 132 is an inclinometer, which provides a measure of pitch, roll and yaw that correspond to rotation angles around x, y and z axes. It is also possible that the user wear-able device 102 includes multiple different types of motion sensors, some examples of which were just described. Depending upon the type(s) of motion sensor(s) used, such a sensor can be used to detect the posture of a portion of a user's body (e.g., a wrist or arm) on which the user-wearable device 102 is being worn.

Figure 2:
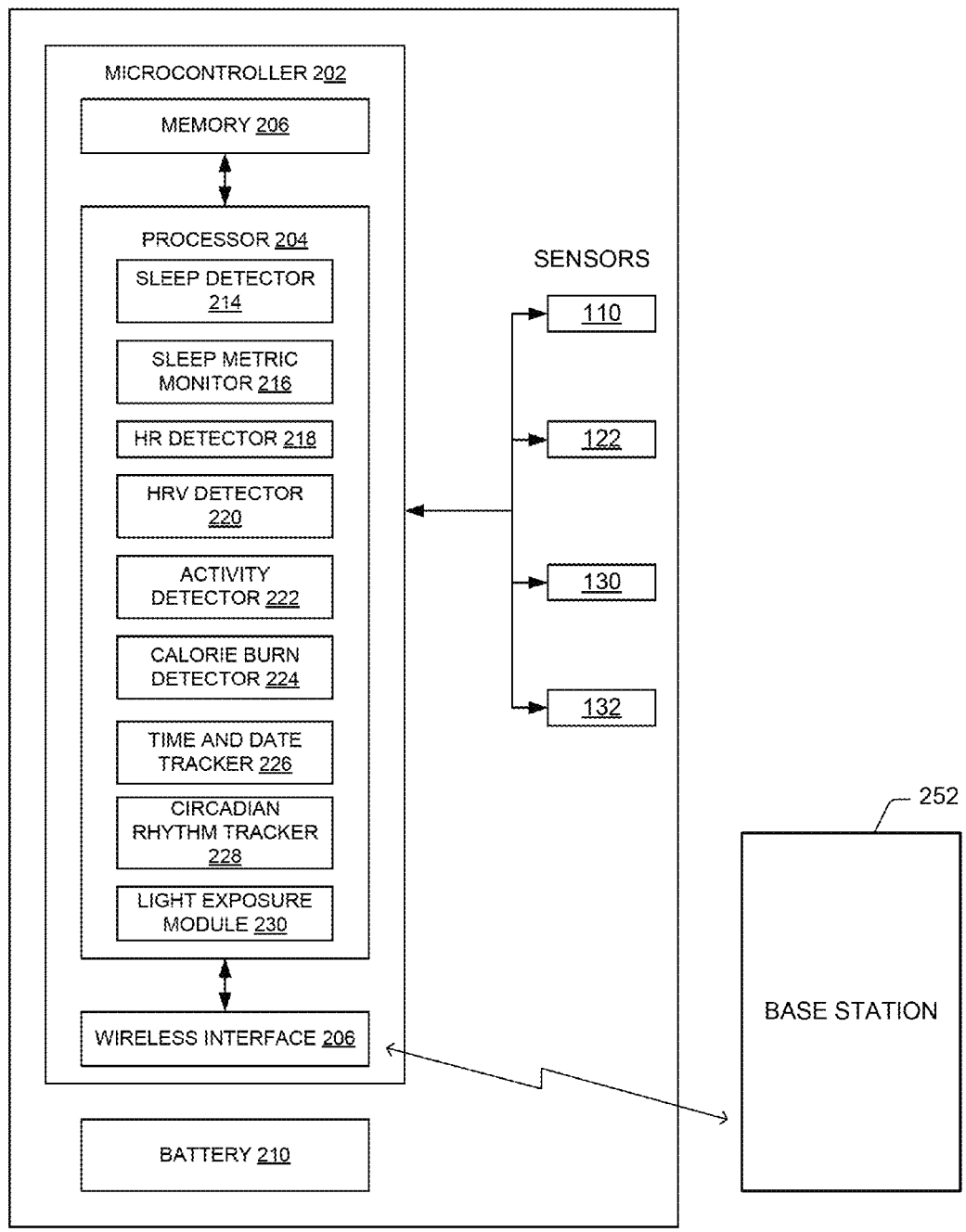
FIG. 2 depicts a high level block diagram of electrical components of the user-wearable device introduced in FIGS. 1A and 1B, according to an embodiment.

FIG. 2 depicts an example block diagram of electrical components of the user-wearable device 102, according to an embodiment. Referring to FIG. 2, the user-wearable device 102 is shown as including a microcontroller 202 that includes a processor 204, memory 206 and a wireless interface 208. It is also possible that the memory 206 and wireless interface 208, or portions thereof, are external the microcontroller 202. The microcontroller 202 is shown as receiving signals from each of the aforementioned sensors 110, 122, 130 and 132. The user-wearable device 102 is also shown as including a battery 210 that is used to power the various components of the device 102. While not specifically shown, the user-wearable device 102 can also include one or more voltage regulators that are used to step-up and or step-down the voltage provided by the battery 210 to appropriate levels to power the various components of the device 102.

Each of the aforementioned sensors 110, 122, 130, 132 can include or have associated analog signal processing circuitry to amplify and/or filter raw signals produced by the sensors. It is also noted that analog signals produced using the aforementioned sensors 110, 122, 130 and 132 can be converted to digital signals using one or more digital to analog converters (ADCs), as is known in the art. The analog or digital signals produced using these sensors can be subject time domain processing, or can be converted to the frequency domain (e.g., using a Fast Fourier Transform or Discrete Fourier Transform) and subject to frequency domain processing. Such time domain processing, frequency domain conversion and/or frequency domain processing can be performed by the processor 204, or by some other circuitry.

The wireless interface 206 can wireless communicate with a base station (e.g., 252), which as mentioned above, can be a mobile phone, a tablet computer, a PDA, a laptop computer, a desktop computer, or some other computing device that is capable of performing wireless communication. The wireless interface 206, and more generally the user wearable device 102, can communicate with a base station 252 using various different protocols and technologies, such as, but not limited to, Bluetooth™, Wi-Fi, ZigBee or ultra-wideband (UWB) communication. In accordance with an embodiment, the wireless interface 206 comprises telemetry circuitry that include a radio frequency (RF) transceiver electrically connected to an antenna (not shown), e.g., by a coaxial cable or other transmission line. Such an RF transceiver can include, e.g., any well-known circuitry for transmitting and receiving RF signals via an antenna to and from an RF transceiver of a base station 252.

The user-wearable device 102 is shown as including various modules, including an a sleep detector module 214, a sleep metric module 216, a heart rate (HR) detector module 218, a heart rate variability (HRV) detector module 220, an activity detector module 222, a calorie burn detector module 224, a time and date tracker module 226, a circadian rhythm tracker module 228, and a light exposure module 230. The various modules may communicate with one another, as will be explained below. Each of these modules 214, 216, 218, 220, 222, 224, 226, 228 and 230 can be implemented using software, firmware and/or hardware. It is also possible that some of these modules are implemented using software and/or firmware, with other modules implemented using hardware. Other variations are also possible. In accordance with a specific embodiments, each of these modules 214, 216, 218, 220, 222, 224, 226, 228 and 230 is implemented using software code that is stored in the memory 206 and is executed by the processor 204. The memory 206 is an example of a tangible computer-readable storage apparatus or memory having computer-readable software embodied thereon for programming a processor (e.g., 204) to perform a method. For example, non-volatile memory can be used. Volatile memory such as a working memory of the processor 204 can also be used. The computer-readable storage apparatus may be non-transitory and exclude a propagating signal.

The sleep detector module 214, which can also be referred to simply as the sleep detector 212, uses signals and/or data obtained from one or more of the above described sensors to determine whether a user, who is wearing the user-wearable device 102, is sleeping. For example, signals and/or data obtained using the outward facing optical sensor 110 and/or the motion sensor 132 can be used to determine when a user is sleeping. This is because people typically sleep in a relatively dark environment with low levels of ambient light, and typically move around less when sleeping compared to when awake. Additionally, if the user's arm posture can be detected from the motion sensor 132, then information about arm posture can also be used to detect whether or not a user is sleeping. The sleep detector 214 can also be used to detect when a user, who is wearing the user-wearable device 102, wakes up, as well as when the user is awake.

The sleep metric detector module 216, which can also be referred to as the sleep metric detector 216, uses signals and/or data obtained from one or more of the above described sensors and/or other modules to quantify metrics of sleep, such as total sleep time, sleep efficiency, number of awakenings, and estimates of the length or percentage of time within different sleep states, including, for example, rapid eye movement (REM) and non-REM states. The sleep metric module 216 can, for example, use signals and/or data obtained from the motion sensor 132 and/or from the HR detector 218 to distinguish between the onset of sleep, non-REM sleep, REM sleep and the user waking from sleep. One or more quality metric of the user's sleep can then be determined based on an amount of time a user spent in the different phases of sleep. Such quality metrics can be displayed on the digital display 108 and/or uploaded to a base station (e.g., 252) for further analysis.

The HR detector module 218, which can also be referred to simply as the HR detector 218, uses signals and/or data obtained from the PPG sensor 122 to detect HR. For example, the PPG sensor 222 can be used to obtain a PPG signal from which peak-to-peak intervals can be detected, which can also be referred to as beat-to-beat intervals. The beat-to-beat intervals, which are intervals between heart beats, can be converted to HR using the equation HR=(1/beat-to-beat interval)*60. Thus, if the beat-to-beat interval=1 sec, then HR=60 beats per minute (bpm); or if the beat-to-beat interval=0.6 sec, then HR=100 bpm. The user's HR can be displayed on the digital display 108 and/or uploaded to a base station (e.g., 252) for further analysis.

The HRV detector module 220, which can also be referred to simply as the HRV detector 220, uses signals and/or data obtained from the PPG sensor 122 to detect HRV. For example, in the same manner as was explained above, beat-to-beat intervals can be determined from a PPG signal obtained using the PPG sensor 122. HRV can be determined by calculating a measure of variance, such as, but not limited to, the standard deviation (SD), the root mean square of successive differences (RMSSD), or the standard deviation of successive differences (SDSD) of a plurality of consecutive beat-to-beat intervals. Alternatively, or additionally, an obtained PPG signal can be converted from the time domain to the frequency domain, and HRV can be determined using well known frequency domain techniques. The user's HRV can be displayed on the digital display 108 and/or uploaded to a base station (e.g., 252) for further analysis.

The activity detector module 222, which can also be referred to simply as the activity detector 222, can determine a type and amount of activity of a user based on information such as, but not limited to, motion data obtained using the motion sensor 132, heart rate as determined by the HR detector 218, light detected using the outwardly facing optical sensor 110, skin temperature as determined by the skin temperature sensor 130, and time of day. The activity detector module 222 can using motion data, obtained using the motion sensor 132, to determine the number of steps that a user has taken with a specified amount of time (e.g., 24 hours), as well as to determine the distance that a user has walked and/or run within a specified amount of time. Activity metrics can be displayed on the digital display 108 and/or uploaded to a base station (e.g., 252) for further analysis.

The calorie burn detector module 224, which can also be referred to simply as the calorie burn detector 222, can determine a current calorie burn rate and an amount of calories burned over a specified amount of time based on motion data obtained using the motion sensor 132, HR as determined using the HR detector 218, and/or skin temperature as determined using the skin temperature sensor 130. A calorie burn rate and/or an amount of calories burned can be displayed on the digital display 108 and/or uploaded to a base station (e.g., 252) for further analysis.

The time and date tracker module 226, which can also be referred to simply as the time and date tracker 226, can keep track of the time of day, date, and/or the like, which are typically tracked by a digital wristwatch. The time and date can be displayed on the digital display 108. Additionally, the time and date tracker module 226 of the user-wearable device can be synced with a similar module of the base station 252. The time and data tracker 226 can provide time of day and date information to the other modules described herein.

The circadian rhythm tracker module 228, which can also be referred to simply as the circadian rhythm tracker 228, uses signals and/or data obtained from one or more of the above described sensors and/or other modules to detect a user's nominal circadian rhythm and deviations therefrom. This can include tracking a user's typical wake up times and bedtimes, but is not limited thereto. The circadian rhythm tracker 228 can also identify changes in a user's circadian rhythm that are recommended to improve a user's sleep and/or life in general. The circadian rhythm tracker 228 can further determine how much time has elapsed (e.g., 1 hour) since a user' woke up, how long it is before a user will likely go to bed (e.g., 30 minutes), and the like. Information about a user's circadian rhythm and/or recommended changes thereto can be displayed on the digital display 108 and/or uploaded to a base station (e.g., 252) for further analysis.

The light exposure module 230 can use information obtained from one or more of the above described sensors and/or other modules to detect a user's exposure to one or more particular wavelengths of light in order to trigger user notifications at appropriate times, wherein such user notifications can inform a user wearing the user-wearable device 102 that they should adjust (e.g., increase or reduce) their exposure to light. For example, the light exposure module 230 can obtain signals and/or data indicative of an amount of blue light detected by the optical sensor 110. Additionally, the light exposure module 230 can obtain information indicative of a user's circadian rhythm and/or recommended changes thereto from the circadian rhythm tracker 228. The light exposure module 230 can also obtain information indicative of when a user most recently woke up, typically wakes up, most recently went to bed, typically goes to bed, and/or the like from the sleep detector 214 and/or the circadian rhythm tracker 228. The light exposure module 230 can compare specific information or metrics to appropriate thresholds, and based on results of the comparisons, can determine when to trigger user notifications. Such thresholds can be defined for an entire population, or can specified for individual users based on their age, weight, lifestyle, and/or the like. It is also possible that thresholds can be adjusted based on signals and/or data obtained from one or more of the above described sensors and/or other modules. The high level flow diagram of FIG. 3 will initially be used to describe techniques that can be used by the light exposure module 230 to identify when user notifications should be provided to a person that is wearing the user-wearable device 102. FIGS. 3A-3C will thereafter be used to describe specific embodiments of the techniques introduced in FIG. 3. More generally, the high level flow diagrams of FIGS. 3, 3A, 3B and 3C are used to describe methods according to various embodiments of the present invention. Information about a user's light exposure and/or recommended changes thereto can be displayed on the digital display 108 and/or uploaded to a base station (e.g., 252) for further analysis.

Figure 3:
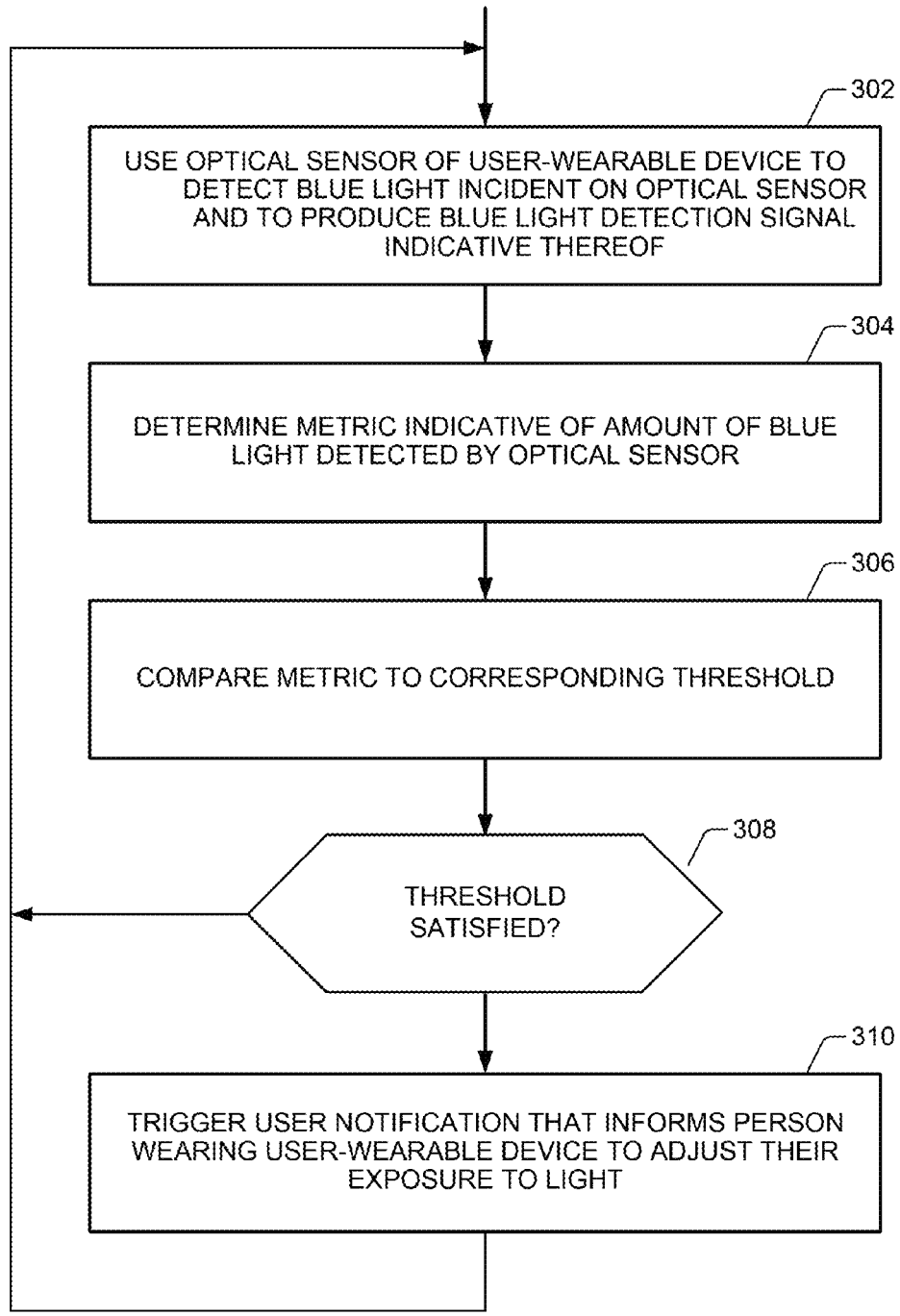
FIG. 3 is a high level flow diagram of a method for use with a user-wearable device, according to an embodiment.
Figure 3A:
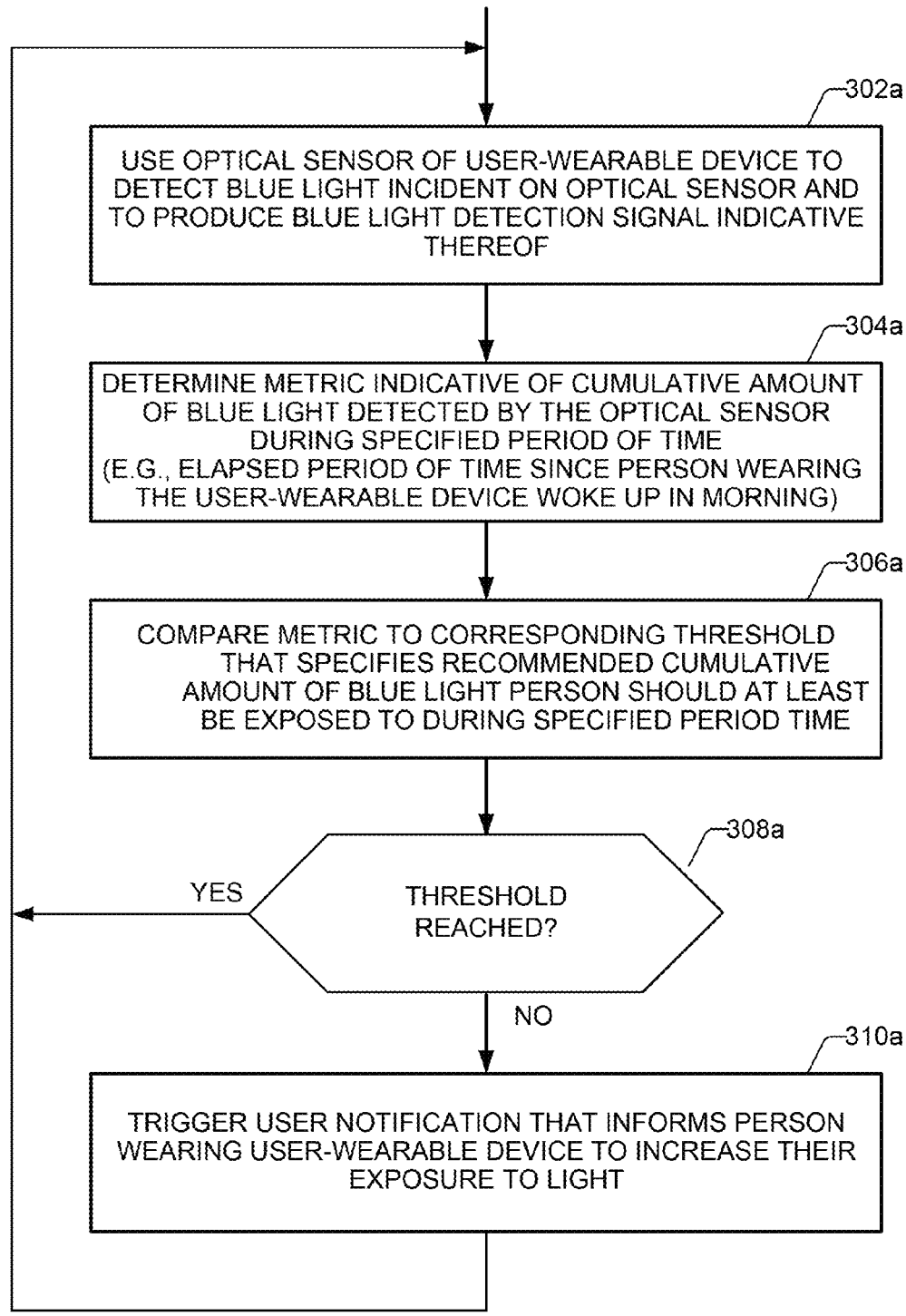
FIG. 3A-3C are high level flow diagrams that provides additional details of some of the steps introduced in FIG. 3, in accordance with various embodiments.
Figure 3B:
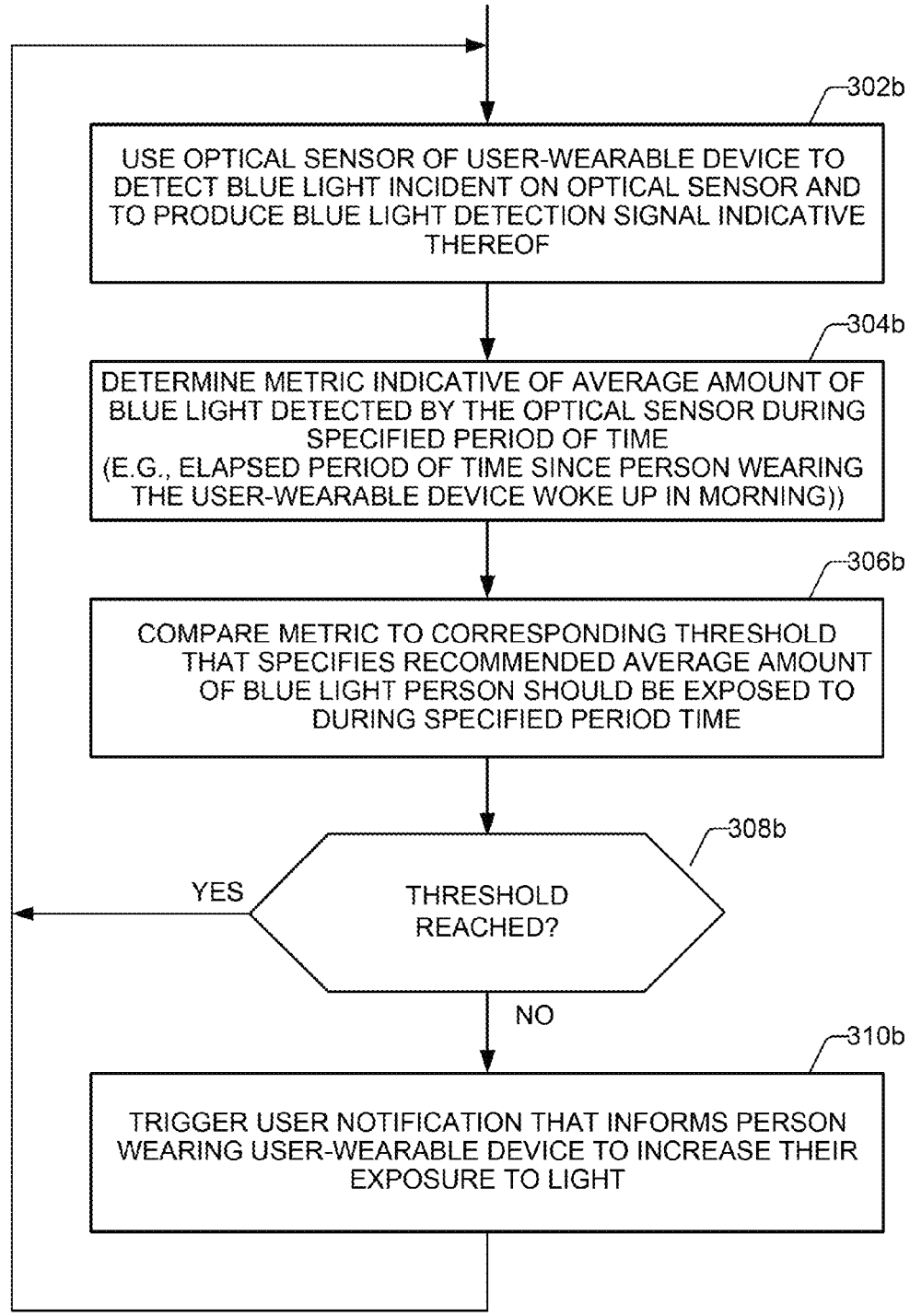
Figure 3C:
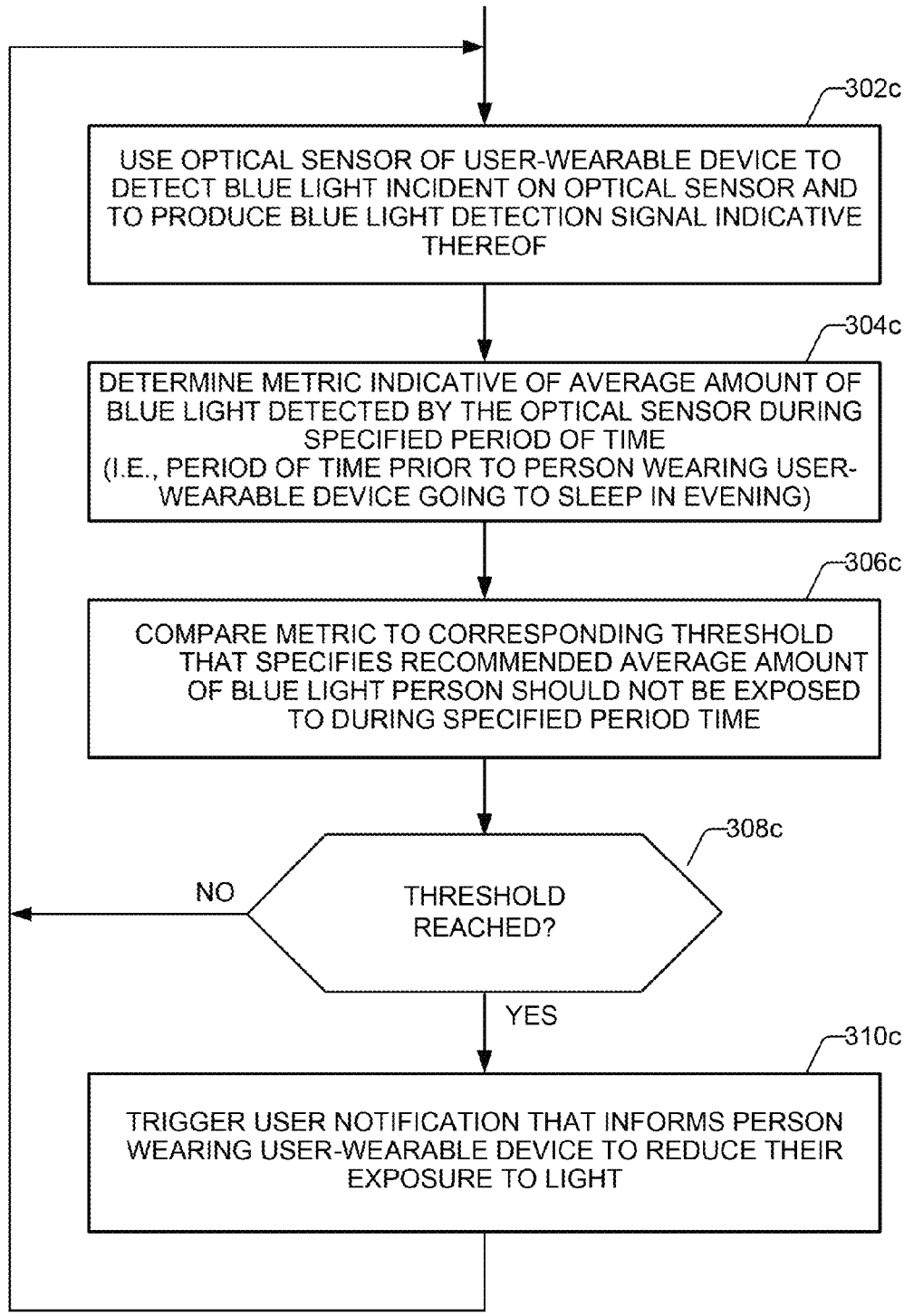
Figure 5:
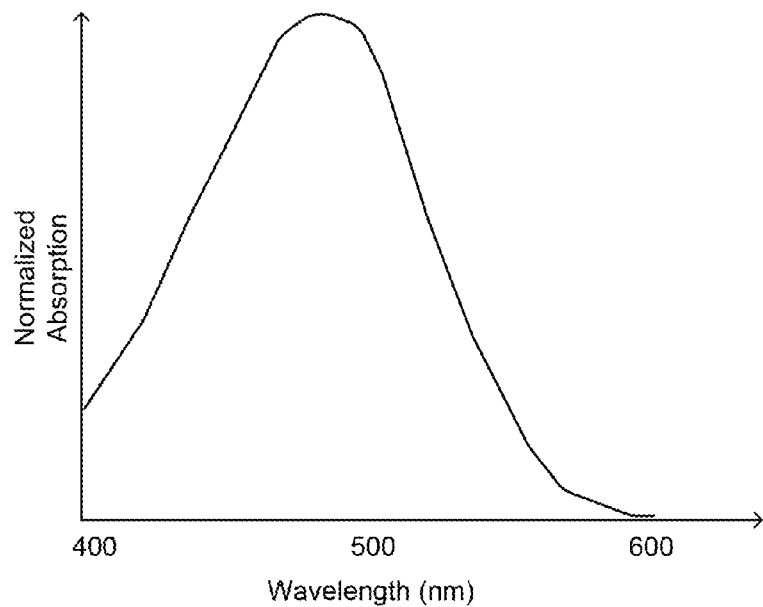
FIG. 5 illustrates the spectral response of mammalian intrinsically photosensitive Retinal Ganglion Cells (ipRGCs).

Referring to the high level flow diagram of FIG. 3, at step 302, an optical sensor (e.g., 110) of a user-wearable device (e.g., 102) is used to detect blue light incident on the optical sensor and to produce a blue light detection signal indicative thereof. By detecting blue light, the optical sensor provides a spectral response that is similar to the spectral response of ipRGCs. Referring briefly to FIG. 5, the graph illustrated therein shows the spectral response of ipRGCs. Preferably, the optical sensor 110 produces a blue light detection signal that emulates the spectral response shown in FIG. 5. As explained above, such an optical sensor can include one or more light detecting elements (also referred to as photodetectors) that is/are covered by a blue organic filter, or a blue inorganic filter, or a combination thereof. The filter can alternatively be made from a plurality of layers of high and low refractive index inorganic dielectric films alternated one above the other to achieve the aforementioned desired spectral response. These are just a few examples of how filters can be used to provide an optical sensor that has a spectral response similar to the spectral response of ipRGCs, which examples are not meant to be all encompassing. Additional exemplary details of an optical sensor that can be used to detect blue light and produce a blue light detection signal indicate thereof were included above in the discussion of the optical sensor 110 with reference to FIG. 1.

Referring again to FIG. 3, at step 304 there is a determination of a metric indicative of the amount of blue light detected by the optical sensor 110. Depending upon the implementation and embodiment, the metric can be indicative of the present level of blue light detected by the optical sensor. Alternatively, the metric can be indicative of a cumulative amount of blue light detected by the optical sensor over a specified period of time, e.g., as will be explained in additional detail below with reference to FIG. 3A. Alternatively, the metric can be indicative of an average amount of blue light detected by the optical sensor over a specified period of time, e.g., as will be explained in additional detail below with reference to FIG. 3B.

At step 306, the metric determined at step 306 is compared to a corresponding threshold, and at step 308 there is a determination of whether the threshold is satisfied (e.g., reached or crossed). The metric and the corresponding threshold can be specified in a unit of illuminance, such as lux or foot candles, but is not limited thereto. It is also possible that an arbitrary unit be used, so long is the threshold(s) is/are scaled accordingly. If the threshold is not satisfied (or is satisfied, depending upon implantation), then flow returns to step 302, as shown in FIG. 3. If the threshold is satisfied (or not satisfied, depending upon implementation), then a user notification is triggered at step 310, wherein the user notification informs the person wearing the user-wearable device that they should adjust their exposure to light. Depending upon the specific threshold and time of day, the user notification can inform a user to increase their exposure to blue light or sunlight. Alternatively, the user notification can inform a user to reduce their exposure to blue light or sunlight. Such user notifications can be textual notifications that are displayed on a digital display (e.g., 108) of a user-wearable device (e.g., 102). Alternatively, or additionally, such user notifications can be pictorial and/or auditory. In specific embodiments where the user notification is displayed on the digital display, a vibratory and/or auditory alert can also be triggered to alert the user to the fact that there is some type of user notification that is being displayed. This way the user will know when they should look at the display of the user-wearable device.

FIG. 3A will now be used to explain specific embodiments that can be used to inform a user when they have not been exposed to enough blue light or sunlight, which can cause adverse effects such as seasonal or non-seasonal depression and low levels of alertness, cognition, reaction time and/or vigilance. The embodiments described with reference to FIG. 3A would most likely be for use in the morning and/or early afternoon. Referring to FIG. 3A, step 302a in FIG. 3A is the same as step 302 discussed above with reference to FIG. 3, and thus need not be described again. Step 304a is a specific implementation of step 304 discussed above with reference to FIG. 3. More specifically, at step 304a there is a determination of a metric indicative of a cumulative amount of blue light detected during a specified period of time. In accordance with an embodiment, the specified period of time is an elapsed period of time since a person wearing the user-wearable device woke up in the morning. The time that the person woke up can be determined by the sleep detector module 214, or can be a programmed time or a time indicated by the user.

Figure 4A:
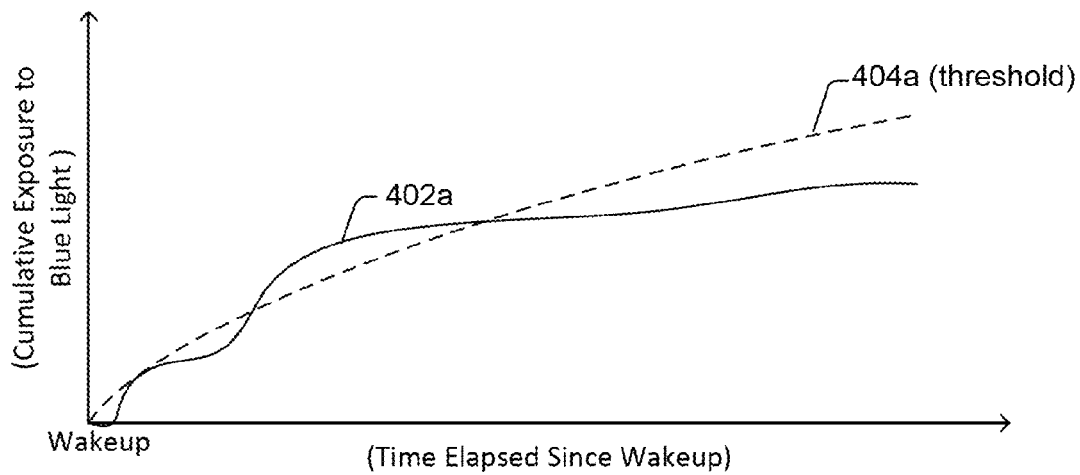
FIG. 4A-4C illustrate exemplary thresholds, defining a line or curve, which can be used in the methods described with reference to FIGS. 3A-3C.
Figure 6:
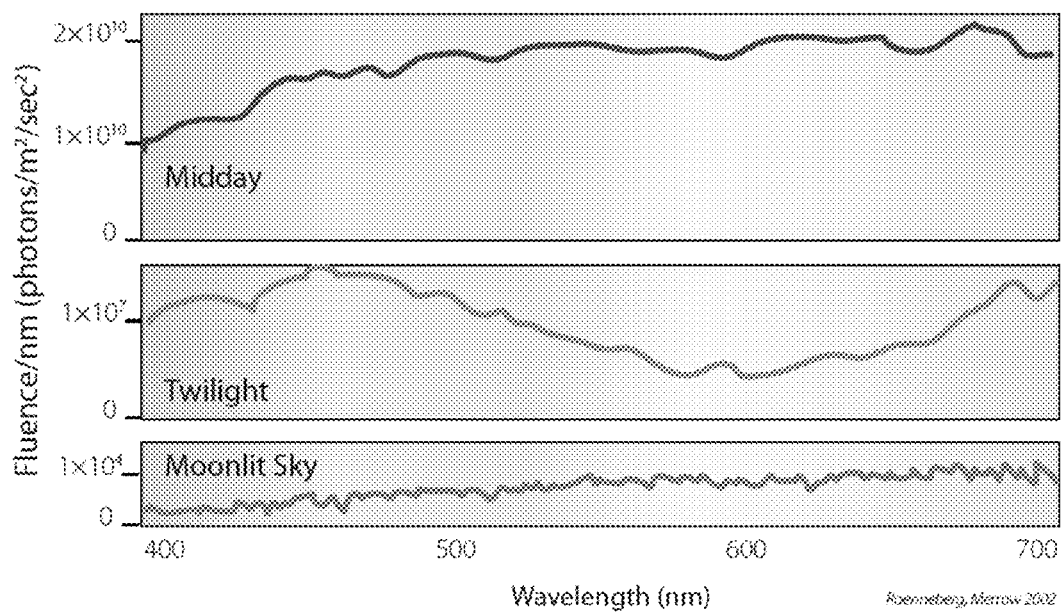
FIG. 6 illustrates the sky spectra at three different times of day, including midday, twilight, and a moonlit nighttime sky.

At step 306a, the metric determined at step 304a is compared to a threshold, and at step 308a there is a determination of whether the threshold was reached. In accordance with an embodiment, the threshold specifies a recommended cumulative amount of blue light that a person should at least be exposed to during a specified period time. The threshold can be a single value that is compared to the metric (indicative of a cumulative amount of blue light detected during a specified period of time) at a fixed time period (e.g., 1 hour) after the user woke up. Alternatively, there can be multiple different threshold levels, each corresponding to a different time period after the user woke up. For example, a first threshold can be compared to a metric indicative of a cumulative amount of blue light detected during the one hour period since the person wearing the user-wearable device woke up; a second threshold can be compared to a metric indicative of a cumulative amount of blue light detected during the two hour period since the person wearing the user-wearable device woke up; . . . and an $n^{th}$ threshold can be compared to a metric indicative of a cumulative amount of blue light detected during the n-hour period since the person wearing the user-wearable device woke up. It is also possible that the threshold defines a line or curve, e.g., as shown in the graph in FIG. 4A. More specifically, referring briefly to FIG. 4A, the solid line 402*a* represents a cumulative amount of blue light detected over time (since the person woke up), and the dashed line 404*a* represents the threshold that specifies a recommended cumulative amount of blue light that a person should at least be exposed to over time (since the person woke up). In such an embodiment, metrics represented by the solid line 402*a* can be continually, or at specific time intervals (e.g., periodically), compared to the threshold levels represented by the dashed line 404*a* in order to perform steps 306*a* and 308*a* shown in FIG. 3A. Referring again to FIG. 3A, if there is a determination at step 308*a* that the threshold is reached, then flow returns to step 302*a*, as shown in FIG. 3A. If the threshold is not reached, then a user notification is triggered at step 310*a*, wherein the user notification informs the person wearing the user-wearable device that they should increase their exposure to light. If the user notification is textual, there is a myriad of different notifications that can be provided, depending upon implementation. For example, the textual user notification can simply inform that user to do one of the following: go outside; get more sunlight; get more light (in general); get more blue light; etc. These are just a few examples, which are not intended to be all encompassing. The reason that a user notification may recommend that a user go outside and/or get more sunlight is that sunlight is an excellent source of the blue light that ipRGCs are primarily responsive to, as can be appreciated from the graphs shown in FIG. 6. Referring briefly to FIG. 6, the graphs shown therein illustrate that sunlight at midday, as well as at twilight, provide high levels of the 480 nm blue light to which ipRGCs are primarily responsive.

Figure 4B:
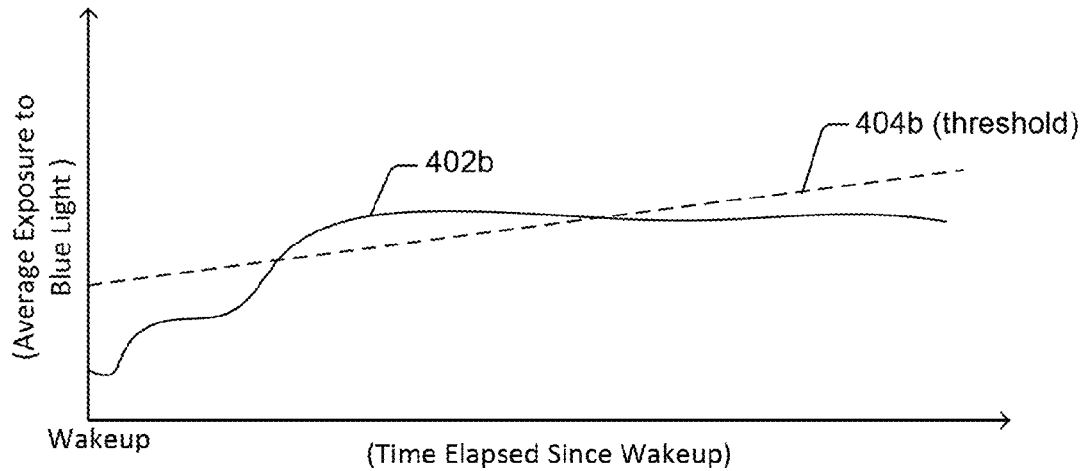

FIG. 3B will now be used to explain other embodiments that can be used to inform a user when they have not been exposed to enough blue light, which as mentioned above, can cause adverse effects. The embodiments described with reference to FIG. 3B would most likely be for use in the morning and/or early afternoon. Referring to FIG. 3B, step 302*b* in FIG. 3B is the same as step 302 discussed above with reference to FIG. 3, and thus need not be described again. Step 304*b* is a specific implementation of step 304 discussed above with reference to FIG. 3. More specifically, at step 304*b* there is a determination of a metric indicative of an average amount of blue light detected during a specified period of time. In accordance with an embodiment, the specified period of time is an elapsed period of time since a person wearing the user-wearable device woke up in the morning. The time that the person woke up can be determined by the sleep detector module 214, or can be a programmed time or a time indicated by the user. In another embodiment, the specified period of time is the most recent N minutes or hours (e.g., the most recent 30 minutes). At step 306*b*, the metric determined at step 304*b* is compared to a threshold, and at step 308*b* there is a determination of whether the threshold was reached. In such embodiments, the threshold used at step 308*a* can be a single value that is compared to the metric (indicative of an average amount of blue light detected during a specified period of time) at a fixed time period (e.g., 1 hour) after the user woke up. Alternatively, there can be multiple different average blue light exposure threshold levels, each corresponding to a different time period after the user woke up. It is also possible that the threshold defines a line or curve, e.g., as shown in the graph in FIG. 4B. More specifically, referring briefly to FIG. 4B, the solid line 402*b* represents an average amount of blue light detected over time (since the person woke up), and the dashed line 404*b* represents the threshold that specifies a recommended average amount of blue light that a person should at least be exposed to over time (since the person woke up). In such an embodiment, metrics represented by the solid line 402*b* can be continually, or at specific time intervals (e.g., periodically), compared to the threshold levels represented by the dashed line 404*b* in order to perform steps 306*b* and 308*b* shown in FIG. 3B. Referring again to FIG. 3B, if there is a determination at step 308*b* that the threshold is reached, then flow returns to step 302*b*, as shown in FIG. 3B. If the threshold is not reached, then a user notification is triggered at step 310*b*, wherein the user notification informs the person wearing the user-wearable device that they should increase their exposure to light. The same or similar user notifications as/to those discussed above with reference to step 310*a* in FIG. 3A can be triggered at step 310*b*.

Figure 4C:
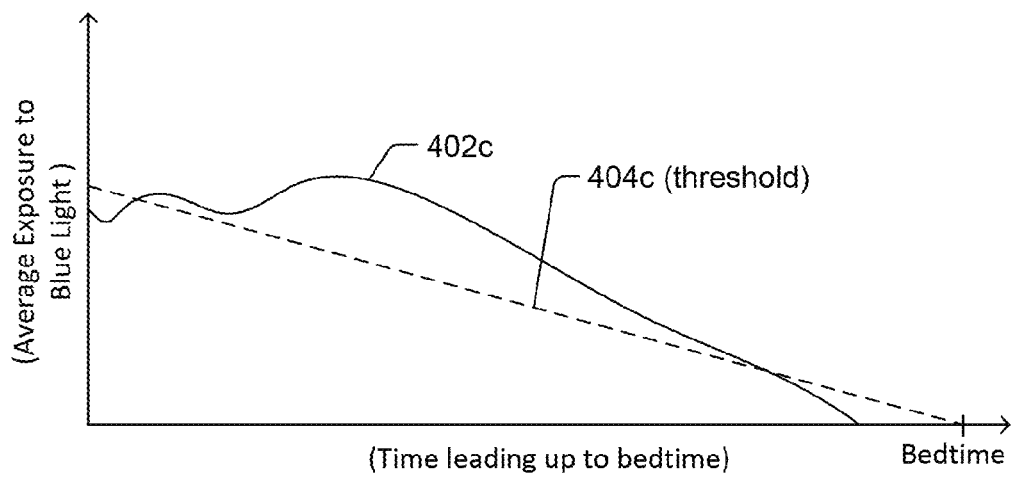

FIG. 3C will now be used to explain specific embodiments that can be used to inform a user when they are being exposed to too much blue light, which can cause adverse effects such as suppressed secretion of melatonin, insomnia and other sleep disorders. There are even studies that suggest that too much exposure to blue light, or too much exposure to blue light at certain times of the day, at linked to diabetes, depression, cancer and cardiovascular problems (many such problems may stem from sleep disorders caused by too much blue light at certain times of day). The embodiments described with reference to FIG. 3C would likely be for use in the evening, and potentially also the late afternoon. Referring to FIG. 3C, step 302*c* in FIG. 3C is the same as step 302 discussed above with reference to FIG. 3, and thus need not be described again. Step 304*c* is a specific implementation of step 304 discussed above with reference to FIG. 3. More specifically, at step 304*c* there is a determination of a metric indicative of an average amount of blue light detected during a specified period of time. In accordance with an embodiment, the specified period of time is a period of time prior to a person wearing the user-wearable device going to sleep in an evening, which can also be referred to as bedtime. The time that the person typically goes to sleep (i.e., the person's typical bedtime) can be determined by the sleep detector module 214, or can be a programmed time or a time indicated by the user. At step 306*c*, the metric determined at step 304*c* is compared to a threshold, and at step 308*c* there is a determination of whether the threshold was reached. In accordance with an embodiment, the threshold specifies a recommended average amount of blue light that a person should not exceed being exposed to during the specified period time. The threshold can be a single value that is compared to the metric (indicative of an average amount of blue light detected during a specified period of time) at a fixed time period (e.g., 1 hour) before the person's bedtime. Alternatively, there can be multiple different threshold levels, each corresponding to a different time period leading up to the person's bedtime. For example, a first threshold can be compared to a metric indicative of an average amount of blue light detected between 3-4 hours before bedtime; a second threshold can be compared to a metric indicative of an average amount of blue light detected between 2-3 hours before bedtime; a third threshold can be compared to a metric indicative of an average amount of blue light detected between 1-2 hours before bedtime; and fourth threshold can be compared to a metric indicative of an average amount of blue light detected during the last hour before bedtime. It is also possible that the threshold defines a line or curve, e.g., as shown in the graph in FIG. 4C. More specifically, referring briefly to FIG. 4C, the solid line 402c represents an average amount of blue light detected over time leading up to bedtime, and the dashed line 404c represents the threshold that specifies a recommended average amount of blue light that a person should not exceed being exposed to leading up to bedtime. In such an embodiment, metrics represented by the solid line 402c can be continually, or at specific time intervals (e.g., periodically), compared to the threshold levels represented by the dashed line 404c in order to perform steps 306c and 308c shown in FIG. 3C. Referring again to FIG. 3C, if there is a determination at step 308c that the threshold is not reached, then flow returns to step 302c, as shown in FIG. 3C. If the threshold is reached, then a user notification is triggered at step 310c, wherein the user notification informs the person wearing the user-wearable device that they should reduce their exposure to light. If the user notification is textual, there is a myriad of different notifications that can be provided, depending upon implementation. For example, the textual user notification can simply inform that user to do one of the following: turn off lights; get less light (in general); get less blue light; etc. These are just a few examples, which are not intended to be all encompassing.

Figure 3D:
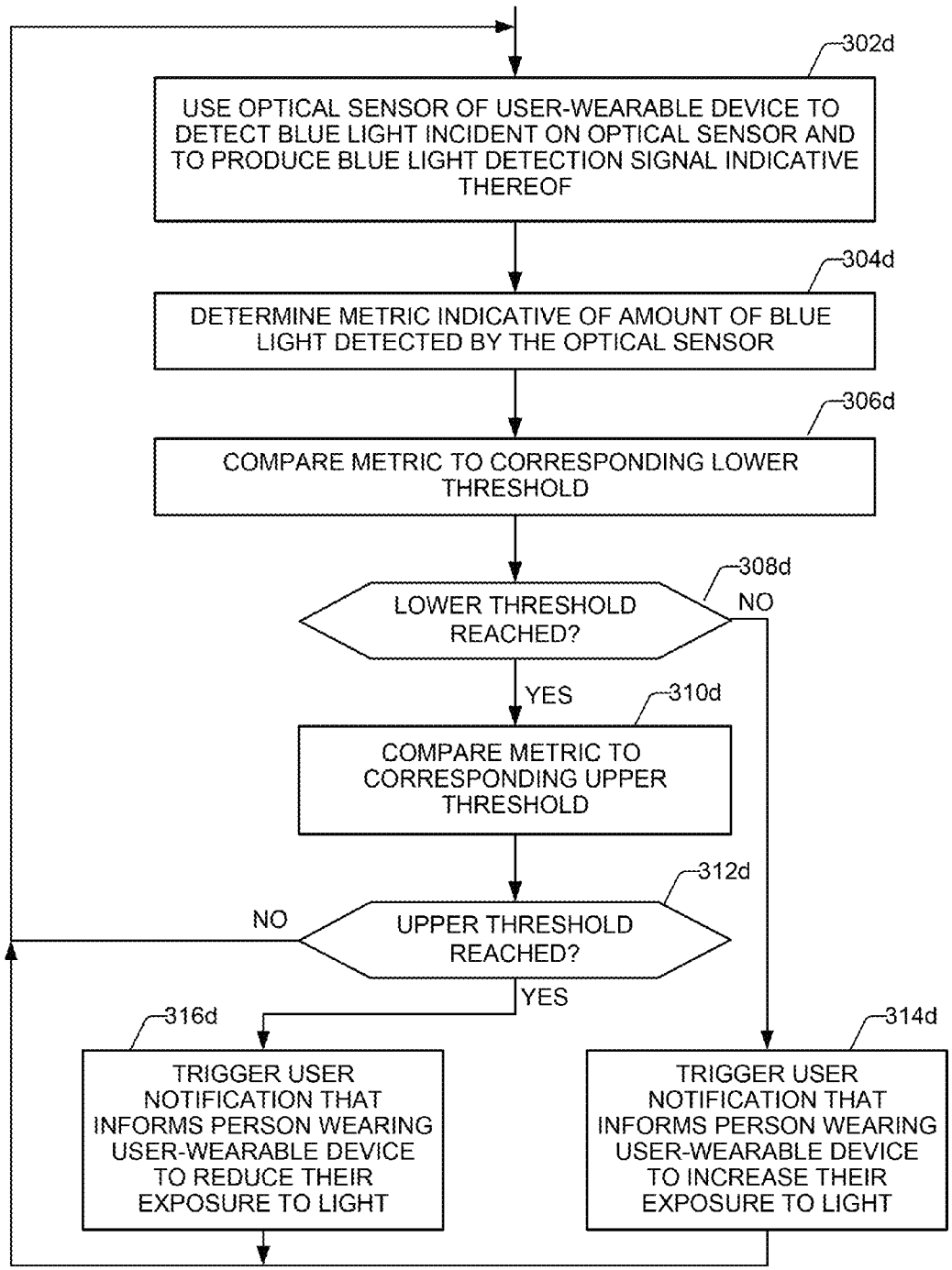
FIG. 3D is a high level flow diagram used to describe embodiments that are a combination of the embodiments described with reference to FIGS. 3A-3C.

It is also possible that combinations of the embodiments described above with reference to FIGS. 3A-3C can be used to determine when to issue user notifications recommending that a user adjust their exposure to light. For example, one of the methods described with reference to FIGS. 3A and 3B can be performed in the morning, and the method described with reference to FIG. 3C is performed in the evening. It is also possible that a method, such as the one summarized in the high level flow diagram of FIG. 3D, be a combination or hybrid of the above described methods. In FIG. 3D there is a lower threshold (referred to in steps 306d and 308d) and an upper threshold (referred to in steps 310d and 312d) that essentially define a preferred blue light range. This range can be the same throughout the day, or more preferably, can change depending upon the time of day. Other combinations of the methods described herein are also within the scope of embodiments of the present invention.

In accordance with certain embodiments, the light exposure module 230 performs the steps described with reference to FIGS. 3, 3A, 3B, 3C and 3D. The light exposure module 230 can communicate with and/or receive information from the various other modules and from one or more of the aforementioned sensors to perform such steps.

Figure 7:
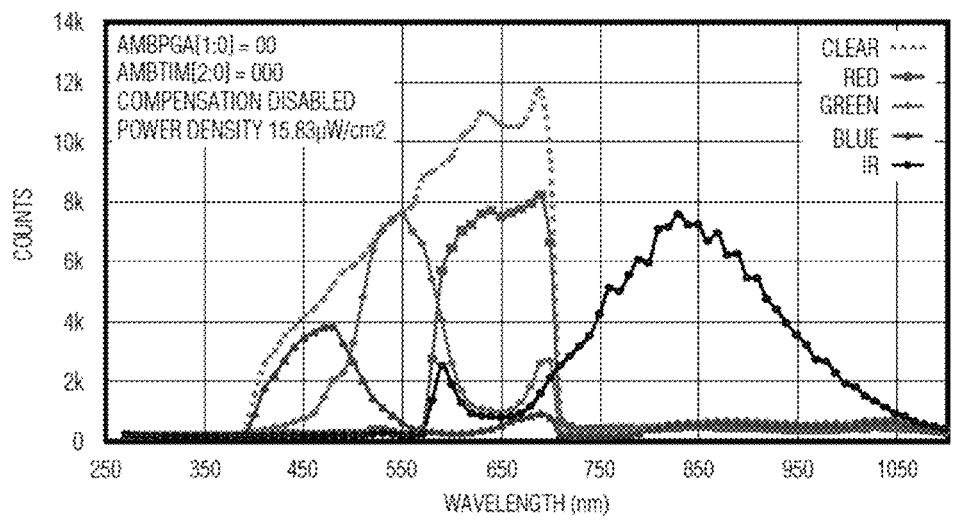
FIG. 7 illustrates the R, G, B and IR responses of an optical sensor.
Figure 8:
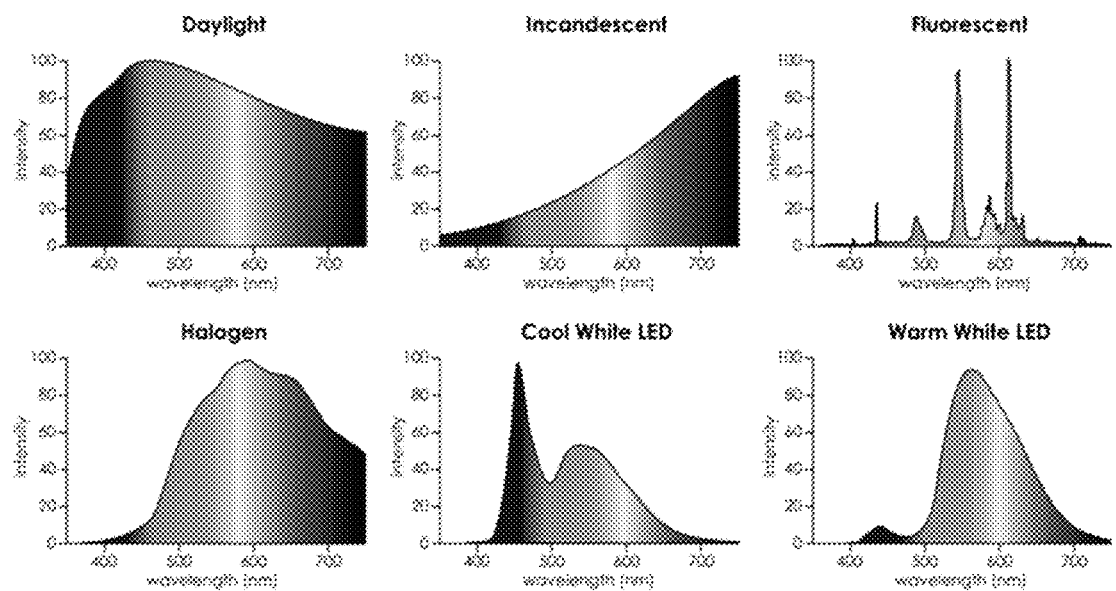
FIG. 8 illustrates the spectra of daylight (i.e., sunlight), and five different types of artificial light.

In the above described embodiments, the outwardly facing optical sensor 110 was generally described as being adapted to produce a blue light detection signal indicative of the amount of blue light detected by the optical sensor 110, and thus, indicative of the response of the user's ipRGCs. It was also mentioned that the optical sensor 110 can be an RGB sensor that produces three separate light detections signals, including a red light detection signal, a green light detection signal and a blue light detection signal. It was also noted that the optical sensor 110 can also be configured to detect IR light, in which case the optical sensor can also produce in IR light detection signal. The graph in FIG. 7 illustrates exemplary R, G, B and IR responses of such an optical sensor. FIG. 8 illustrates the spectra of daylight (i.e., sunlight), and five different types of artificial light, including incandescent, fluorescent, halogen, cool white light emitting diode (LED), and warm white LED. It can be appreciated from FIG. 8 that each type of light includes a unique spectra that distinguishes its spectra from other types of light. For example, fluorescent light includes substantially no red and infrared light, especially compared to the levels of red and infrared light included in daylight and incandescent light. For another example, halogen light includes substantially no blue light, especially compared to the levels of blue light included in daylight and cool white LED light. For a further example, daylight include similar levels of blue and green light, whereas cool white LED light include significantly more blue light than green light. In accordance with certain embodiments of the present invention, the light exposure module 230, or some other module, receives a blue light detection signal plus one or more of a red light detection signal, a green light detection signal and an IR light detection signal, and determines therefrom, whether a user is outside (where they are exposed to daylight) or inside. More specifically, information about the spectra of various types of light, or simply sunlight versus non-sunlight, can be stored within the device 102 and used to perform such determinations. Based on such a determination, when user notifications are provided to recommend that a user adjust their exposure to light, such user notifications can be more specific to the present situation. For example, if it is daytime when the light exposure module 230 determines that the user should expose themselves to more blue light, and it is determined that a user is inside (e.g., because the device determines that the primary source of detected light is fluorescent light, or more generally, not sunlight), then the light exposure module 230 may recommend that the user go outside or get more sunlight. This is just one example, which is not intended to be all encompassing.

In FIGS. 1A and 1B the user-wearable device 102 was shown as being a wrist-wearable device. The user-wearable device can alternatively be a device that can be clipped to a portion of a user's body or to an article of clothing. Other variations are also possible.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto. While various embodiments have been described above, it should be understood that they have been presented by way of example, and not limitation. It will be apparent to persons skilled in the relevant art that various changes in form and detail can be made therein without departing from the spirit and scope of the invention. The breadth and scope of the present invention should not be limited by any of the above-described exemplary embodiments, but should be defined only in accordance with the following claims and their equivalents.

What is claimed is:

1. A method for use by a user-wearable device including a display and an optical sensor, the method comprising:
    (a) using the optical sensor of the user-wearable device to detect blue light that is incident on the optical sensor and to produce a blue light detection signal indicative thereof;
    (b) determining, in dependence on the blue light detection signal, a metric indicative of one of an average or cumulative amount of blue light detected by the optical sensor during a specified period of time;

(c) comparing the metric to a corresponding threshold to determine whether the metric reaches the threshold; and (d) triggering a textual user notification in dependence on results of the comparing the metric to the corresponding threshold, wherein the textual user notification is displayed on the display of the user-wearable device and provides a person wearing the user-wearable device with a recommendation to one of increase or decrease their exposure to light.

2. The method of claim 1, wherein the metric determined at step (b) is indicative of the cumulative amount of blue light detected by the optical sensor during the specified period of time.

3. The method of claim 2, wherein:
the specified period of time is an elapsed period of time since a person wearing the user-wearable device woke up in the morning;
the corresponding threshold specifies a recommended cumulative amount of blue light that a person be exposed to during the specified period time; and
step (d) comprises triggering the textual user notification if the metric does not reach the threshold, wherein the textual user notification, which is displayed on the display of the user-wearable device, provides the person wearing the user-wearable device with a recommendation to increase their exposure to blue light or sunlight.

4. The method of claim 1, wherein the metric determined at step (b) is indicative of the average amount of blue light detected by the optical sensor during the specified period of time.

5. The method of claim 4, wherein:
the corresponding threshold specifies a recommended average amount of blue light that a person should at least be exposed to during the specified period time; and
step (d) comprises triggering the textual user notification if the metric does not reach the threshold, wherein the textual user notification, which is displayed on the display of the user-wearable device, provides the person wearing the user-wearable device with a recommendation to increase their exposure to blue light or sunlight.

6. The method of claim 4, wherein:
the specified period of time is a period of time prior to an evening bedtime of a person wearing the user-wearable device;
the corresponding threshold specifies a recommended average amount of blue light that a person should not exceed being exposed to during the specified period time;
step (d) comprises triggering the textual user notification if the metric reaches the threshold, wherein the textual user notification, which is displayed on the display of the user-wearable device, provides the person wearing the user-wearable device with a recommendation to reduce their exposure to blue light or sunlight.

7. The method of claim 1, wherein in order to alert the person wearing the user-wearable device that the textual user notification is being displayed on the display of the user-wearable device, the triggering the textual user notification at step (d) further comprises at least one of the following:
triggering an audible user notification;
triggering a visible user notification; or
triggering a vibratory user notification.

8. The method of claim 1, further comprising:
using the optical sensor, or a further optical sensor, to detect one or more additional colors of the light, besides blue light, and to produce one or more additional light detection signals indicative thereof; and
determining, based on the blue light detection signal and at least one of the one or more additional light detection signals, whether a person wearing the user-wearable device is inside or outside;
wherein, in response determinations that the person wearing the user-wearable device is inside and has been exposed to less blue light than an amount specified by the corresponding threshold, the textual user notification triggered at step (d), which is displayed on the display of the user-wearable device, provides the person wearing the user-wearable device with a recommendation to go outside.

9. A user-wearable device, comprising:
an optical sensor that detects blue light that is incident on the optical sensor and produces a blue light detection signal indicative thereof;
a display;
a light exposure module that
determines, in dependence on the blue light detection signal, a metric indicative of one of an average or cummulative amount of blue light detected by the optical sensor during a specified period of time;
compares the metric to a corresponding threshold to determine whether the metric reaches the threshold; and
triggers a textual user notification in dependence on results of the comparison of the metric to the corresponding threshold, wherein the textual user notification is displayed on the display of the user-wearable device and provides a person wearing the user-wearable device with a recommendation to one of increase or decrease their exposure to light.

10. The user-wearable device of claim 9, further comprising:
a band that straps the user-wearable device to a person's wrist.

11. The user-wearable device of claim 9, wherein the display comprises a digital display that displays the textual user notification.

12. The user-wearable device of claim 11, further comprising:
an audible or vibratory alert that informs a person that a user notification is being displayed on the digital display.

13. The user-wearable device of claim 9, wherein:
the optical sensor includes one or more light detecting elements that is/are covered by a blue filter.

14. A method for use by a user-wearable device including an optical sensor, the method comprising:
(a) using the optical sensor of the user-wearable device to produce a light detection signal having a spectral response similar to that of intrinsically photosensitive Retinal Ganglion Cells (ipRGCs);
(b) determining, in dependence on the light detection signal, a metric indicative of one of an average or cumulative amount of blue light detected by the optical sensor during a specified period of time;
(c) comparing the metric to a corresponding threshold to determine whether the metric reaches the threshold;
(d) determining, in dependence on results of the comparing the metric to the corresponding threshold and a present time of day, whether to display a textual user notification that provides a person wearing the user-wearable device with a recommendation to one of increase or decrease their exposure to light; and (e) selectively displaying a textual user notification that informs a person wearing the user-wearable device to one of increase or decrease their exposure to light, based on results of the determining at step (d).

15. The method of claim 14, wherein the textual user notification, which is selectively displayed at step (e), is selected from the group consisting of
a textual user notification that recommends increased exposure to blue light or sunlight; and
a textual user notification that recommends decreased exposure to blue light or sunlight.

16. A user-wearable device, comprising:
an optical sensor that produces a light detection signal having a spectral response similar to that of intrinsically photosensitive Retinal Ganglion Cells (ipRGCs);
a digital display; and
a light exposure module that
determines, in dependence on the light detection signal, a metric indicative of one of an average or cumulative amount of blue light detected by the optical sensor during a specified period of time;
compares the metric to a corresponding threshold to determine whether the metric reaches the threshold;
determines, in dependence on results of the comparison of the metric to the corresponding threshold and a present time of day, whether to provide a textual user notification that informs a person wearing the user-wearable device to one of increase or decrease their exposure to light; and
selectively causes to be displayed, on the digital display, a textual user notification that informs a person wearing the user-wearable device to one of increase or decrease their exposure to light.

17. The user-wearable device of claim 16, wherein the light exposure module selectively causes to be displayed, on the digital display, a textual user notification selected from the group consisting of:
a textual user notification that recommends increased exposure to blue light or sunlight; and
a textual user notification that recommends decreased exposure to blue light or sunlight.

18. The user-wearable device of claim 17, further comprising:
a band that straps the user-wearable device to a person's wrist.

* * * * *